United States Patent [19]
Criton et al.

[11] Patent Number: 5,800,356
[45] Date of Patent: Sep. 1, 1998

[54] ULTRASONIC DIAGNOSTIC IMAGING SYSTEM WITH DOPPLER ASSISTED TRACKING OF TISSUE MOTION

[75] Inventors: Aline Laure Criton; Thanasis Loupas, both of Seattle, Wash.

[73] Assignee: Advanced Technology Laboratories, Inc., Bothell, Wash.

[21] Appl. No.: 865,340

[22] Filed: May 29, 1997

[51] Int. Cl.⁶ .................................................. A61B 8/12
[52] U.S. Cl. ................................ 600/441; 600/455
[58] Field of Search ........................... 600/455, 441, 600/443, 450, 437

[56] References Cited

U.S. PATENT DOCUMENTS

| | | |
|---|---|---|
| 4,501,277 | 2/1985 | Hongo ............................. 600/441 |
| 5,195,521 | 3/1993 | Melton, Jr. et al. ............... 600/450 |
| 5,215,093 | 6/1993 | Miyazaki et al. ................. 600/455 |
| 5,435,310 | 7/1995 | Sheehan et al. .................. 600/437 |
| 5,513,640 | 5/1996 | Yamazaki et al. ................ 600/455 |
| 5,622,174 | 4/1997 | Yamazaki ......................... 600/441 |

*Primary Examiner*—Marvin M. Lateef
*Assistant Examiner*—Maulin Patel
*Attorney, Agent, or Firm*—W. Brinton Yorks, Jr.

[57] ABSTRACT

A method and apparatus are presented for tracing the border of tissue through temporally acquired scanlines comprising the steps of reducing noise in the scanlines, producing a map of tissue edges from the scanlines, denoting a tissue border to be traced, and using velocity information corresponding to tissue edges to trace the denoted border.

41 Claims, 6 Drawing Sheets

5,800,356

ULTRASONIC DIAGNOSTIC IMAGING SYSTEM WITH DOPPLER ASSISTED TRACKING OF TISSUE MOTION

This invention relates to ultrasonic diagnostic imaging systems and, in particular, to ultrasonic diagnostic imaging systems in which motion depicted in ultrasonic images is tracked through the assistance of ultrasonic velocity information.

One of the primary uses of medical diagnostic ultrasound is the diagnosis of cardiac function and disease. Echocardiography revolves around the functioning of the heart and the diagnosis of abnormal conditions of cardiac performance and pathology. Of significant interest to the cardiologist in making these diagnoses is clear delineation of the heart structure itself, and in particular the motion of the well-defined heart muscle as it cyclically pumps blood. But many patients are what are known as "difficult patients," meaning that the patient's physiology impedes the creation of sharply defined images from strong, clear echo returns. In those and other, more normal situations, the echocardiographer is limited to diagnosing from echocardiograms of poorly defined cardiac structures. To aid in diagnoses in these situations, ultrasound systems facilitate the tracing of the outlines of cardiac structures on the displayed echocardiogram by the echocardiographer, generally with a joystick or trackball. Quantified measures and analyses can then be performed based upon the dimensions and measurement of the outlined structures. But such tracing can be a painstaking task, since the heart is constantly contracting and relaxing and valves are continually opening and closing. For a complete and accurate diagnosis, it may be necessary to define the structures of the heart in every echocardiogram throughout the cardiac cycle so that the heart muscle is continually defined while it is in motion. Realtime cardiac images are produced at a nominal rate of 30 images per second or more, presenting the echocardiographer with a daunting number of images with image structures to trace. It would be desirable, of course, for the ultrasound system to outline the structures of the heart automatically, and to maintain such outlines by tracking these structures automatically as they are engaged in the dynamics of contraction and relaxation, opening and closing.

In accordance with the principles of the present invention, an ultrasonic diagnostic imaging system is provided in which moving structures in a realtime ultrasonic image sequence are automatically tracked by use of velocity information. In a constructed embodiment the velocity information is derived from ultrasonic Doppler signals. Such automatic tracking enables the heart wall to be outlined or traced continually as it moves with the motion of the beating heart cycle. A preferred method for automatically tracing a moving structure in a realtime image sequence comprises the steps of detecting the edges of structures in the images, identifying an edge which is to be tracked or traced, and tracking or tracing the identified edge during its motional sequence with the use of velocity information concerning the identified edge.

In an illustrated embodiment, the borders of the heart wall are identified and traced in an M-mode sequence by use of the velocity characteristics of the beating heart. This embodiment leads to a number of useful diagnostic tools, such as analysis of the mean velocity of the heart wall or measurement of the velocity gradient across the heart muscle.

Figure 1:
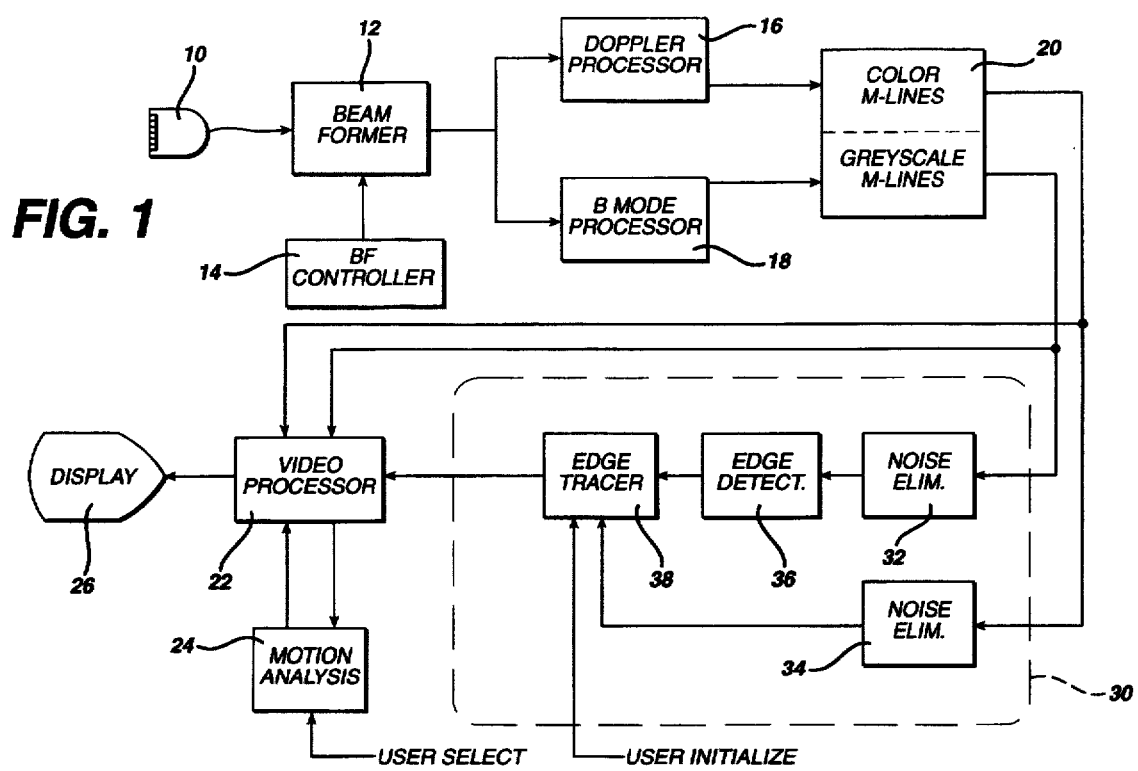
FIG. 1 is a block diagram of an ultrasonic diagnostic imaging system constructed in accordance with the principles of the present invention.

Referring first to FIG. 1, an ultrasonic diagnostic imaging system constructed in accordance with the principles of the present invention is shown in block diagram form. An ultrasonic array probe 10 is operated under control of a beamformer 12 to transmit ultrasonic waves into the body of a patient and receives echoes returning from the body in response to those waves. The beamformer 12 is controlled by a beamformer controller 14 which controls the time of activation of the probe transducer array elements to steer and focus a transmitted beam. The beamformer is also controlled to appropriately delay and sum received echo signals to form received beams of coherent echoes along each desired scanline.

The echoes from the received scanlines may then be processed in a variety of ways. One way is by means of a B mode processor 18, which detects the echo amplitudes. The echo amplitudes may then be displayed spatially as a greyscale or B mode image of the body. Another processing technique is by means of a Doppler processor, which processes ensembles of scanlines from a common location to detect the Doppler shift of moving blood and other tissues along the scanlines. The Doppler signals can be continually received from a sample volume in the body and displayed in a spectral Doppler display. A second means of display is a colorflow display, in which the Doppler signals are spatially overlaid for display with a greyscale image, thereby depicting flow parameters within the structures of the greyscale image.

In accordance with one aspect of the present invention, the detected and processed echo signals are displayed in a time-motion or M-mode display format. In an N-mode display a one dimensional image, a single scanline termed an A-line, is repetitively scanned and displayed over time. The resultant display reveals changes occurring along the scanline location with time. M-mode displays can be formed using either Doppler or greyscale scanlines. In the system of FIG. 1, Doppler scanlines produced by the Doppler processor 16 are stored as color M-lines in storage device 20, and greyscale scanlines produced by the B mode processor 18 are stored as greyscale M-lines in the storage device 20. The M-mode display is most useful for displaying structures in the body which are moving, such as the beating heart, as this movement can be seen in the time-displaced sequence of scanlines of the display.

The color M-lines stored in the storage device 20 may be read from the device and converted into video signals by a video processor 22, then displayed as a color M-mode display on a display 26. The greyscale M-lines may also be applied to the video processor 22 for display as a greyscale M-mode display.

In accordance with the principles of the present invention, the edges or borders of structures in the greyscale scanlines are traced by a motion tracker 30. The motion tracker 30 uses the Doppler signals to track the movement of moving structures such as blood cells and other tissue in the greyscale scanlines. The motion tracker first removes extraneous artifacts and noise from the greyscale scanlines by means of a noise eliminator 32 and, optionally, a noise eliminator 34 eliminates noise from the Doppler scanlines. The greyscale scanlines then undergo edge detection by an edge detector 36, which identifies the locations of edges or boundaries of structures along the scanlines. Finally, the edges or boundaries depicted in a sequence of scanlines are traced with an edge tracer 38. The edge tracing is initiated by user initialization, whereby a user points to one point along the edge which is to be traced. The edge tracer then traces the edge of which the identified point is a part. It does this through use of the velocity data of the Doppler information. The Doppler information provides data as to the velocity at locations along the greyscale scanline, including the boundary point identified by the user. By knowing the time interval which lapsed between the acquisition of each greyscale scanline, and the velocity and direction of motion of an identified boundary point, the system can compute the location to which the boundary point has moved by the time of the subsequently acquired scanline. The system then looks for the boundary point in the vicinity of the computed position and produces a trace connecting the points of the two scanlines. In this way the motion tracker 30 can continuously track moving structures or structure boundaries from one scanline to the next, and can trace or outline them in the M-mode display.

The trace defined by the edge tracer 38 is applied to the video processor in concert with the greyscale M-lines, where the trace is overlaid over the M-mode display to define the traced edge or border or other characteristic in the display. The trace can also be overlaid over the temporally corresponding color M-mode display.

Once the border of a structure such as the heart wall has been defined by edge tracing, a number of quantified measurements can be made of the now precisely delineated structure. Such quantified measures are performed by a motion analysis module 24 as described below, in which the computation of measures such as mean velocities or velocity gradients are discussed.

Figure 2:
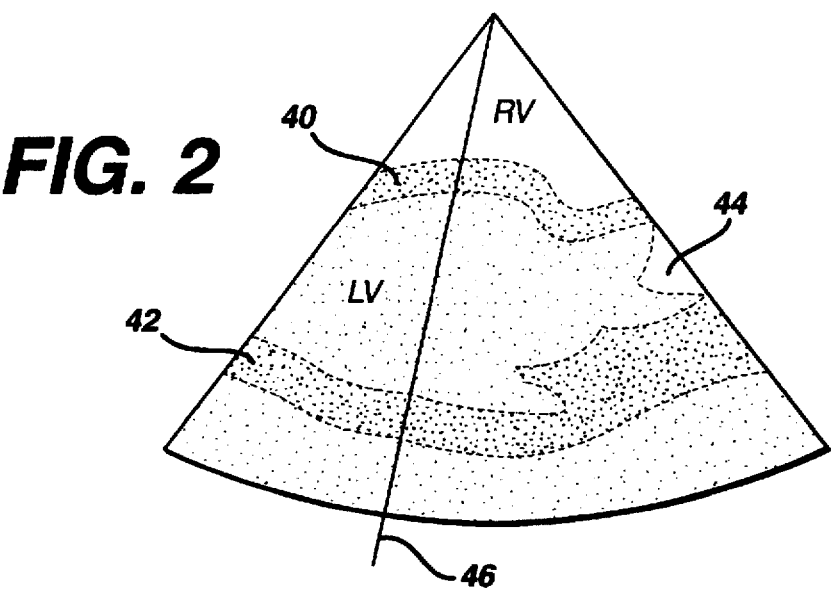
FIG. 2 is a two dimensional image of the left ventricle of the heart with an M-line cursor across the heart chamber.

An understanding of the operation of the system of FIG. 1 may be had with reference to the following drawings. FIG. 2 illustrates a two dimensional ultrasound image of the heart. Typically a sector image of the heart is produced with a phased array probe, although curved and linear array probes may also be used. At the top of the image is a portion of the right ventricle, marked RV in the drawing. A septum 40 separates the right ventricle from the left ventricle LV. The chamber of the left ventricle is bounded by the posterior wall 42. At the right side of the left ventricle is the mitral valve 44.

Figure 3:
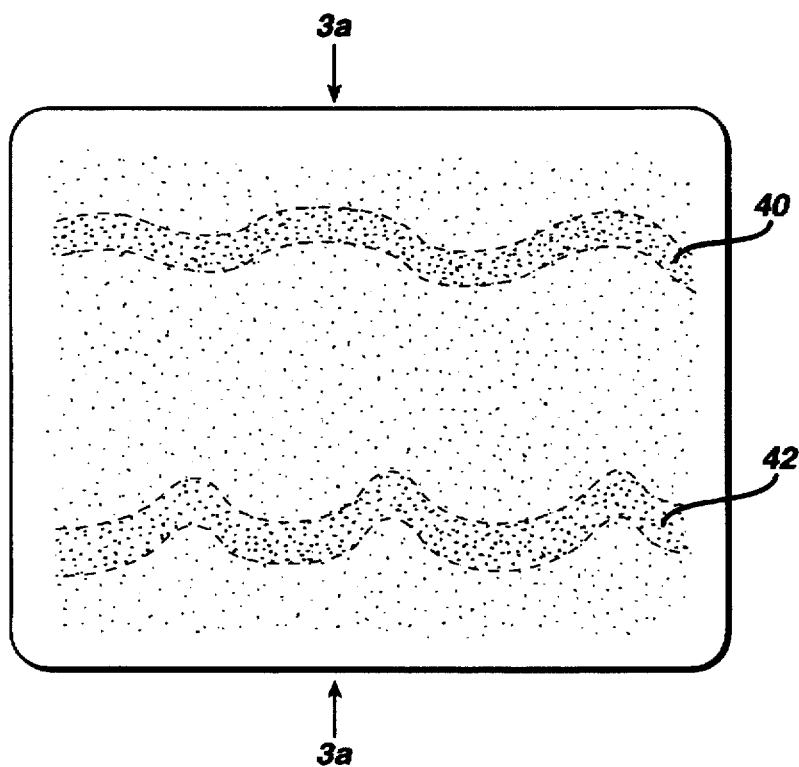
FIG. 3 is a greyscale M-mode display acquired from the M-line location in FIG. 2.
Figure 3A:
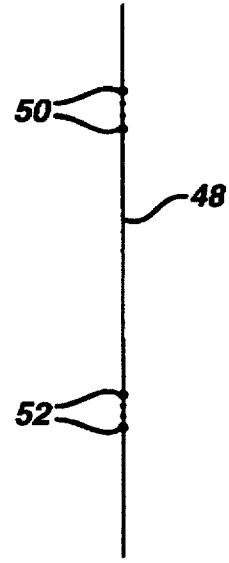
FIG. 3a represents one M-line of the M-mode display of FIG. 3.

Extending from the apex of the image and across the right and left ventricles is an M-mode cursor 46. The M-mode cursor marks the scanline of the two dimensional (2D) image which is repetitively scanned and reproduced to form an M-mode image as shown in FIG. 3. An M-mode image is formed by repetitively scanning the same spatial scanline and reproducing each new scan of the scanline alongside the previous scanlines. Thus, the M-mode image is a time sequence of one dimensional images of a single A-line. The benefit provided by such a display is that the image reveals the motion of tissues and tissue boundaries intersected by the single scanline. In the present example, as the heart beats the left ventricle will cyclically contract, then relax. As the left ventricle contract, the septum 40 and the posterior wall will move closer to each other. And as the left ventricle relaxes these two boundaries of the left ventricle will move apart again. This cyclical motion is revealed in the M-mode display of FIG. 3, where the septum 40 and the posterior wall are seen to periodically approach each other and move apart again. Since tissue boundaries tend to return relatively strong echoes, the boundaries of the septum 40 and the posterior wall 42 will be defined by strong echo returns 50, 52 in each scanline. FIG. 3a, for instance, illustrates the strong echo returns by dots on a single scanline 48, one of many such scanlines that are returned from along the location of the M-mode cursor 46. In FIG. 3a the smaller dots between the strong echo returns 50, 52 represent relatively weaker echo returns from the blood pool within the left ventricle (between the dots 50, 52), and from the right ventricle above the septum 40 (50) and the abdominal tissue below the posterior wall 42 (52).

In accordance with the principles of the present invention, the ultrasound system of FIG. 1 automatically traces one or more of the borders in the H-mode display of FIG. 3. First, the preferred embodiment performs the optional step of noise elimination on the greyscale data of the M-mode display. Any of a number of noise reduction techniques may be employed, such as filtering the greyscale signals or threshold elimination of low level noise or averaging a number of consecutively received M-lines to form each M-line of the M-mode display. However, the present inventor have found a preferable noise reduction technique to be the mathematical morphologic operations of dilation and erosion. This technique is described in the article Haralick et al., "Image Analysis Using Mathematical Morphology" in IEEE Trans. Pattern Anal. and Machine Intell., vol. PAMI-9, (July 1987), which provides a number of examples of mathematical operands which may be use in erosion and dilation. Dilation and erosion are performed along each M-line from the minimum depth of the scanline to the maximum depth of the scanline using the dilation equation $$A(i,j) = \max_{i-\Delta \le k \le i+\Delta}(A(k,j))$$

followed by the erosion equation of $$A(i,j) = \min_{i-\Delta \le k \le i+\Delta}(A(k,j))$$

for each point i along each of j M-lines. Dilation and erosion will remove much of the unwanted noise from the greyscale data such as speckle artifacts and noise in the blood pool of the heart. Each M-line is thus smoother with decreased noise, but without loss of the sharpness of the edges of tissue defined by the greyscale data.

The second step is to develop an "edge map" of the edges of tissue boundaries represented by the greyscale M-line data. A variety of techniques may be used to detect tissue edges, such as detecting transitions between successive data points above a certain level, or differentiating the M-line data. A preferred technique is to use an algorithm which detects edges in the greyscale data by computing the variance of the mean value in a sliding window applied to each M-line from the minimum depth to the maximum depth of each scanline. The preferred algorithm is illustrated in FIG.

4, which is a succession of summation functions Θ (60) and squaring functions ( )² (62), ending in a comparison (subtraction) computation 64. In the preferred algorithm each summation function is of the form $$\Sigma = \frac{1}{(2*\Delta + 1)} \sum_{k=i-\Delta}^{k=i+\Delta} (A(k,j))$$

and each squaring function is of the form $$( )^2 = (A(i,j))^2$$

Figure 4:
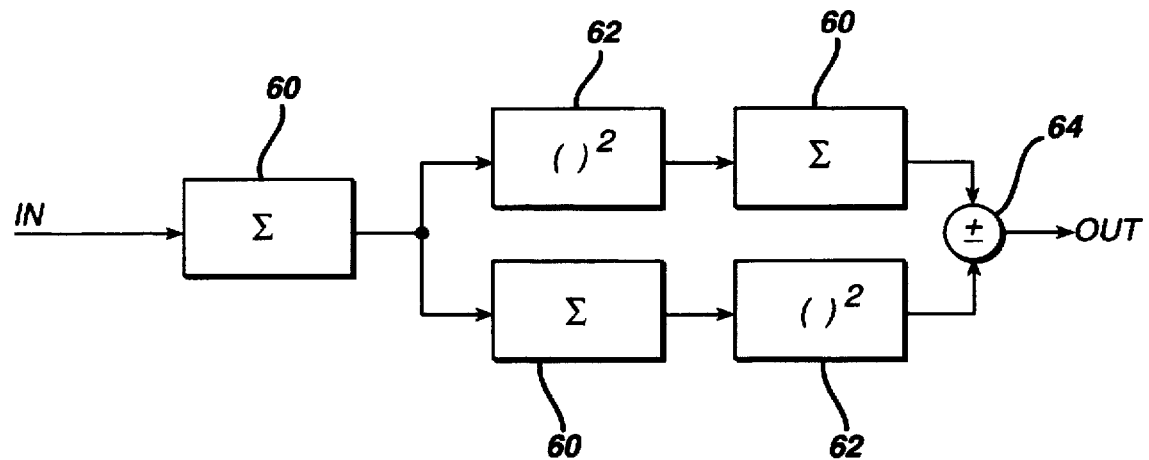
FIG. 4 is a block diagram illustrating a preferred edge detection technique for the ultrasound system of FIG. 1.
Figure 5A:
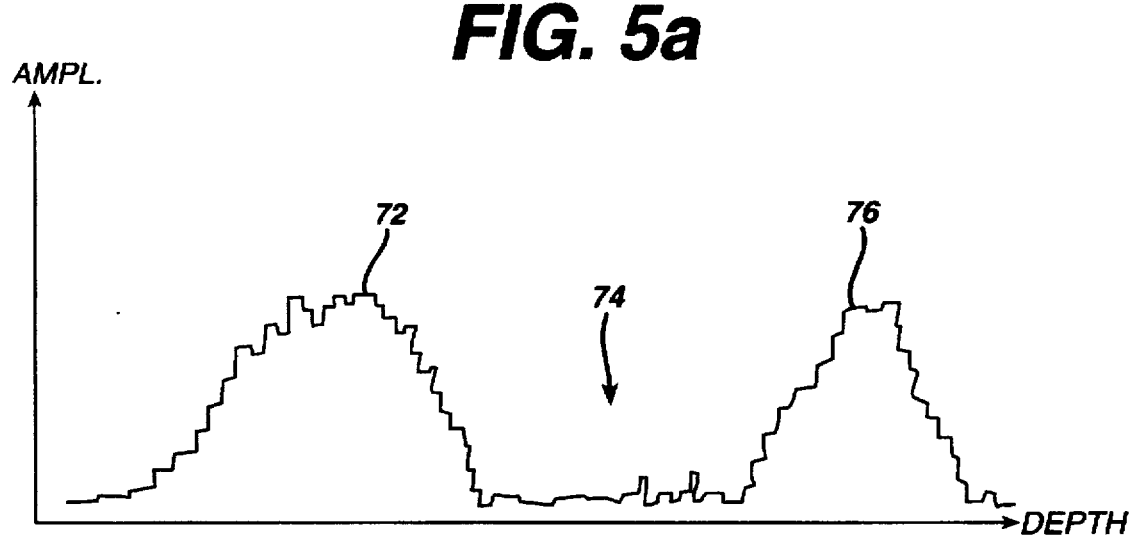
FIGS. 5a–5c are plots illustrating the operation of the preferred edge detection technique of FIG. 4.
Figure 5B:
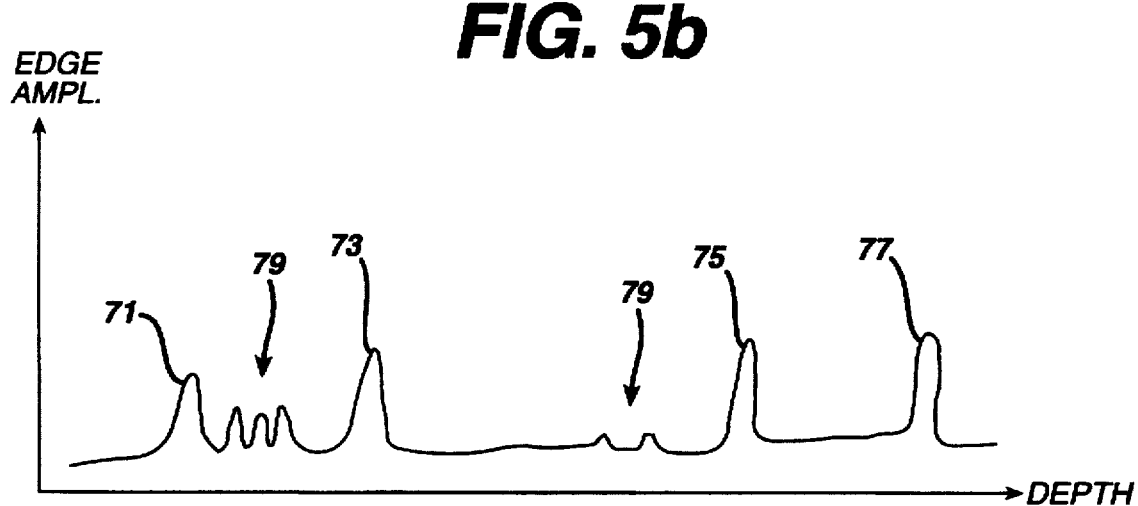

The resolution of the edge map is a function of the size of the window 2Δ of successive data points upon which the algorithm is performed, with a smaller window producing a relatively large number of sharply defined edges and a larger window producing a relatively smaller number of more broadly defined edges. For example, suppose that the data values of the data points of one M-line are as shown in FIG. 5a, which represents the amplitudes of the data points proceeding from the minimum depth to the maximum depth. In this plot the first peak 72 represents data points returned from the septum 40 of FIG. 2 or 3, the second peak 76 represents data points returned from the posterior wall 42 of these drawings, and the region 74 between these two peaks represents data points returned from the blood pool of the left ventricle. When a window of three successive data points is used in the algorithm of FIG. 4 to produce the edge map, an edge map for the M-line such as that shown in FIG. 5b is produced. In this plot the peaks 71 and 73 are the leading and trailing edges of the septum 70 of FIG. 5a, and the peaks 75 and 77 are the leading and trailing edges of the posterior wall 76 of FIG. 5a. The smaller peaks 79 represent smaller transition in the data values from the septum and blood pool.

Figure 5C:
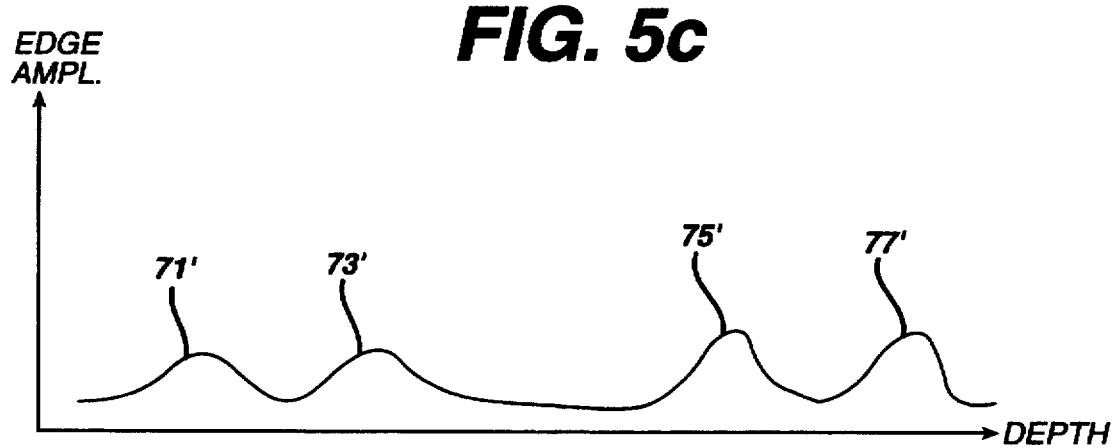

When a wider window such as five or six data point is used for the window, a more broadly defined group of edge peaks are produced as illustrated by FIG. 5c, in which peaks 71' and 73' are the edges of the septum 72 and peaks 75' and 77' are the edges of the posterior wall. Experimentation with a number of different window sizes and M-mode data sets has led the present inventors to prefer a smaller window of three data points for the edge detection algorithm of FIG. 4.

Figure 8:
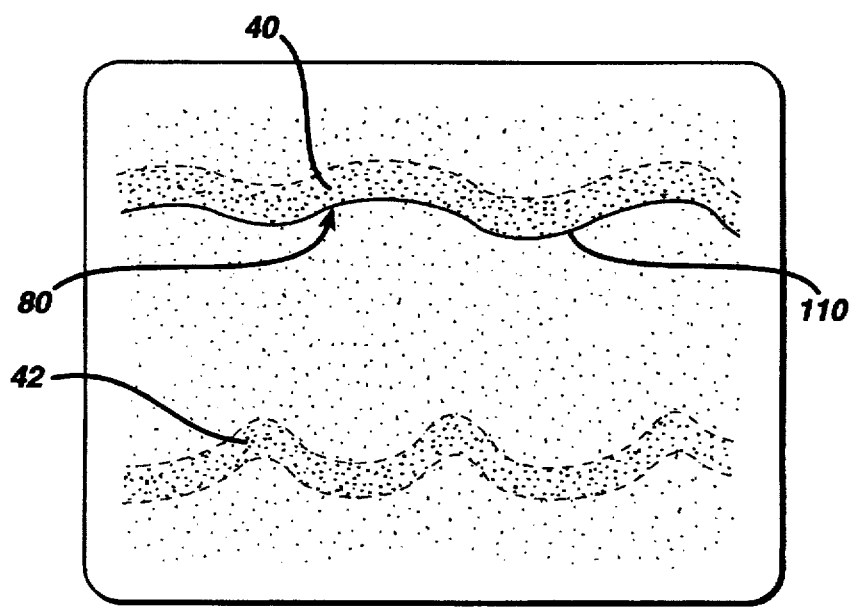
FIG. 8 illustrates the tracing of the heart wall in a greyscale M-mode display in accordance with the present invention.

The next step is to identify a point on an edge which is to be traced by the edge tracker. This is shown in FIG. 8, where an arrow cursor 80 is manipulated over the M-mode display until the arrow is pointing at one point on an edge. In this example the arrow cursor 80 is pointing at the inner border of the septum 40. When the arrow cursor is positioned as desired, the user presses a control on the system to actuate the edge tracer 38, which traces the edge selected by the user.

Figure 6:
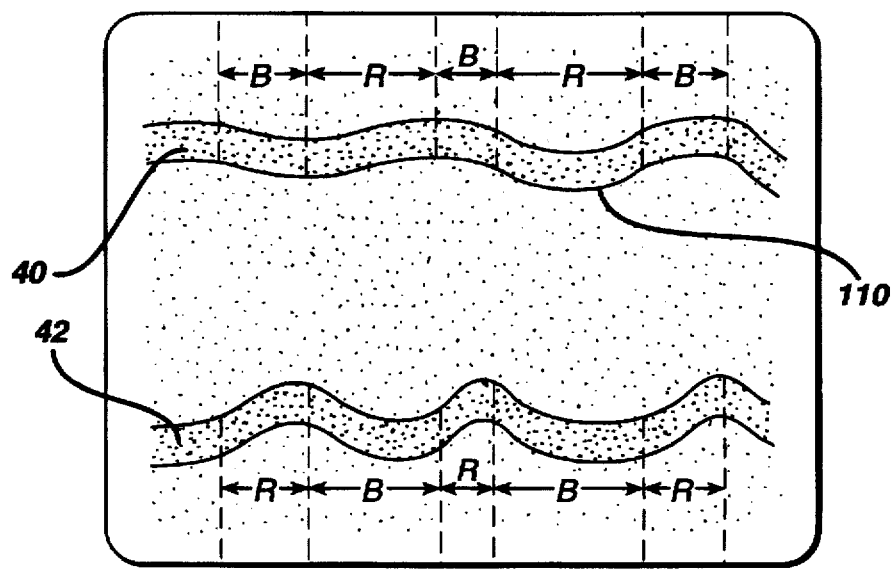
FIG. 6 is a color M-mode display correlated to the greyscale M-mode display of FIG. 3.

In accordance with the principles of the present invention, the edge indicated by the user in the M-mode display is traced using a corresponding map of ultrasonic velocity data. An example of a velocity data map is shown in FIG. 6, which represents a color M-mode display. The color M-mode display of FIG. 6 is produced by the ultrasound system in an interleaved fashion with the M-lines of the M-mode display of FIG. 8. For instance, a pulse is transmitted along the M-mode cursor 46 and echoes are returned from the scanline and their amplitudes detected and displayed as one M-line in the greyscale M-mode display of FIG. 8. A succession of further scanlines are repetitively acquired from along the M-mode cursor over time as a Doppler ensemble of scanlines. The ensemble of scanlines is Doppler processed to detect the velocity of motion at each point along the M-mode cursor at substantially the same time as the time of acquisition of the greyscale M-line. The echoes used to produce the greyscale M-line can of course also be Doppler processed as one of the ensemble of Doppler lines. The ensemble of Doppler lines can also be acquired both before and after the time of acquisition of the greyscale M-line. The succession of lines of velocity data lines can be mapped in the same manner as the M-mode display as indicated in FIG. 6, in which each new line of velocity data is displayed next to the previously acquired line of velocity data, and with color coding of the direction of the motion, hence the term color M-mode display. When the M-mode cursor intersects a chamber of the heart as does the cursor 46, the color M-mode display will vary in color with the direction of the motion of blood and the heart walls. When blue is used for the color of motion away from the transducer and red for the color of motion toward the transducer, the color M-mode display will appear as alternating bands of blue and red as indicated by the alternating B and R bands indicated in the drawing. Since opposite walls of the heart are constantly moving in opposite directions relative to the transducer, i.e., both simultaneously toward the center of the chamber or both simultaneously away from the center of the chamber, the opposite walls will exhibit opposite colors on the same vertical scanline in the color M-mode display. The color M-mode display of FIG. 6 comprises a velocity map corresponding to the greyscale M-mode display of FIG. 8.

Figure 7:
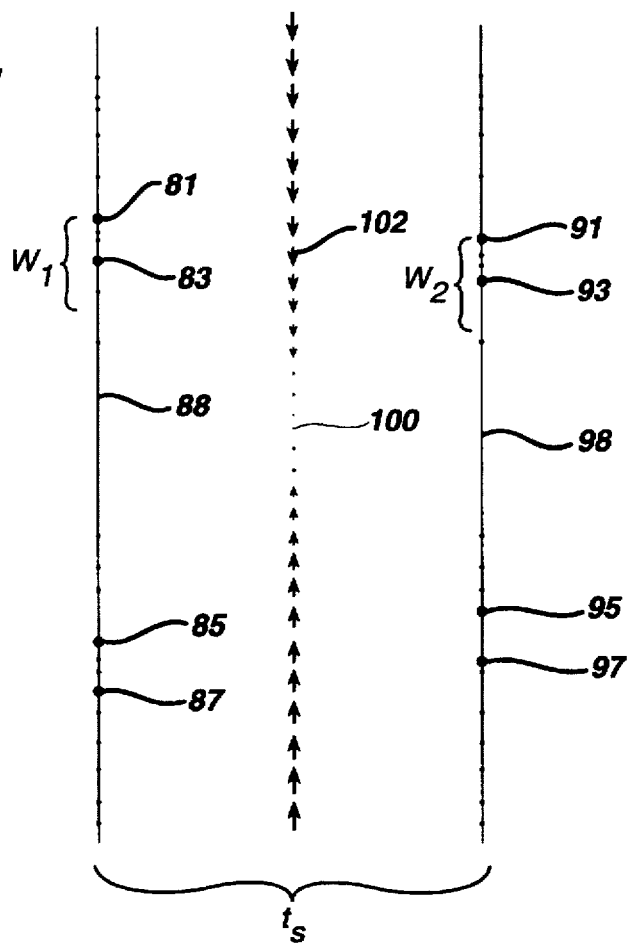
FIG. 7 illustrates the tracking of moving tissue structure in accordance with the principles of the present invention.

The velocity information of the color M-mode display is used to track the location of edges in the greyscale M-mode display as the edges appear at different depths along the M-line from one M-line to another as illustrated by FIG. 7. In this drawing scanlines 88 and 98 represent successively acquired M-lines of a greyscale M-mode display. The large dots 81 and 83 represent detected outer and inner edges of the septum 40 of FIG. 8, and the large dots 85 and 87 represent detected inner and outer edges of the posterior wall 42 of FIG. 8. The second greyscale M-line 98 is acquired after a time interval $t_s$ from the time of acquisition of M-line 88, and its edge map identifies outer and inner edges 91,93 of the septum and inner and outer edges 95,97 of the posterior wall. Between the times of acquisition of these greyscale M-lines, a color Doppler M-line 100 is acquired and processed. Since the heart is contracting during these times the opposite walls of the heart are moving toward each other as depicted by the arrows on the color M-line 100. The arrows are larger in the vicinity of the heart walls at the top and bottom of the color M-line, depicting greater velocities at these locations. In the center of the heart there is little or no motion along the color M-line, as indicated by the dots without arrows in the center of the color M-line 100.

Suppose that the user has pointed the arrow cursor 80 at the inner edge of the septum as shown in FIG. 8. When the greyscale M-line (or edge map line) 88 is so designated, the arrow cursor 80 is pointing at septum inner edge dot 83. The edge tracker 38 now produces a trace to the location of the septum inner edge on the adjacent greyscale line. To do this the edge tracker must identify the inner edge of the septum on the adjacent greyscale M-line. It does this by observing the velocity at the location of inner edge dot 83, which is the velocity value of velocity arrow 102 on the color M-line 100. As the velocity arrow 102 indicates, the velocity of the inner edge of the septum is moving toward the center of the heart chamber (down in the drawing) at this time. The quantified value of the velocity arrow will provide both speed and direction. This velocity is multiplied by the time interval $t_s$ between greyscale lines, yielding a displacement value. The system now has computed that the inner septum edge on line 98 should be displaced downward by the calculated displacement from the corresponding location of the inner edge 83 on line 88. Moving down M-line 98 by this displacement, the system finds inner edge dot 93 on the next M-line 98.

In a constructed embodiment the edge tracker 30 follows an edge from one M-line to the next by use of this technique, but with the added benefit of a window function. This window function is indicated by bracket $W_1$ for M-line 88, which is centered around the edge dot 83 which the system is tracking. By calculating the velocity times time displacement value shown above, the system relocates the window function to the displaced bracket location $W_2$ as shown for M-line 98. The system then identifies an edge of the edge map which is within the window $W_2$ as the edge which is being tracked.

The system of the present invention proceeds in the above manner to track the indicated edge from one greyscale M-line to the next, using the velocity data to compute the new location of the edge in each successive M-line. The technique of the present invention may also be used to track the interior region of tissue such as inside the myocardial wall, enabling the motion of the heart muscle to be defined by a tracing. In a constructed embodiment the edge is tracked both forward and backward in time through the M-mode display. For example, if the arrow cursor 80 is pointing at edge 93, the location of edge 83 in the previous line can be computed using the interval $t_r$, and the velocity of velocity arrow 102 but with its sign (direction) reversed. The finished edge tracing will appear as a highlighted line 110 drawn over the M-mode display in FIG. 8.

The ability to track an edge either forward or backward allows erroneous tracings to be corrected. The greater the distance over which an edge is traced, the greater the possibility that the tracing will move to an adjacent image border. This raises the possibility of the endpoint of a long tracing being on a border other than the desired border. To overcome this condition, the user can point to the desired border at one end of the image and execute a tracing which proceeds forward in time through the image. Then the user can point to the desired border at the other end of the image and execute a tracing which proceeds backward in time through the image. Since both traces are likely to be accurate near their starting points and less so at their end points, the two tracings can be combined on a weighted basis, with the weighting being a function of the proximity of each trace to its starting point. The weighted average of the two traces will generally be an accurate trace of the desired border.

Figure 9:
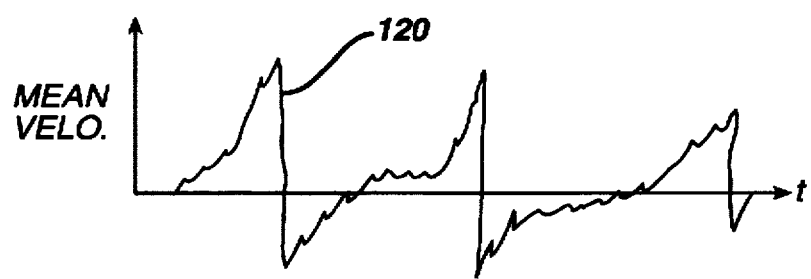
FIG. 9 is a graph of the mean heart wall velocity produced from the color M-mode data of FIG. 6 in accordance with the principles of the present invention.

The edge tracing can be displayed over the color M-mode display as shown in FIG. 6, since the color M-mode display corresponds to the greyscale M-mode display. In FIG. 6 the user has used the ultrasound system of the present invention to trace four edges, the inner and outer borders of both the septum 40 and the posterior heart wall 42. With the borders of the heart walls thus delineated, several quantified measures of cardiac performance can be readily calculated. For instance, the color pixels of a heart wall on each vertical color Doppler line between the tracings can be summed or averaged to compute the instantaneous or mean heart wall velocity. An exemplary plot 120 of the mean velocity of the heart wall which is computed in this manner is shown in FIG. 9 in correspondence with the color M-mode display of FIG. 6. Alternatively, the velocity gradient along each vertical color Doppler line between the tracings can be computed to produce a quantified measure of the velocity gradient across the heart wall. Other quantified measures of heart performance will be readily apparent to those skilled in the art.

It will be appreciated that tissue boundaries can also be identified in color M-mode images by transitions in color, hue, brightness or intensity. Consequently, the present invention can be practiced directly with color M-mode images to trace borders defined in the images and using the velocity information of the images to assist the tracking of image tissue characteristics.

Figure 10:
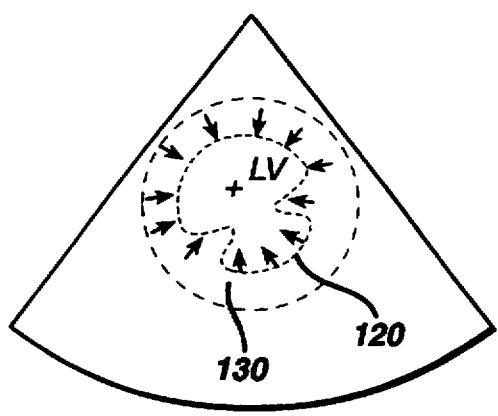
FIG. 10 illustrates the application of the principles of the present invention to two dimensional greyscale images.

The tracing technique of the present invention can also be used to follow the motion of the heart wall from one 2D image to another as shown in FIG. 10. This drawing depicts a short axis view of the heart muscle 130, with the heart wall 120 repetitively moving toward the "+" in the center of the chamber and outward again with each contraction and relaxation of the heart. The velocities of each segment of the heart wall, depicted by the arrows in the drawing around the heart muscle, are computed from Doppler velocity scanning and processing. Since the arrows are arrayed in a radial pattern, several different scanning directions may be needed to overcome the angle sensitivity of the Doppler beam. The velocities around the heart wall are then used to track the heart wall as it moves inward and outward during the cyclic beating of the heart.

The principles of the present invention can also be applied to tracking moving tissue in three dimensional ultrasonic images. In the case of three dimensional images, it will be appreciated that the tracking of moving tissue can occur in any of the three x, y, or z directions, enabling tracing from one voxel to the next in all three dimensions. The three dimensional images can be either greyscale images or M-mode images for which velocity information can be obtained.

What is claimed is:

1. In an ultrasonic diagnostic imaging system, a method for tracking a characteristic of moving tissue in time sequential ultrasonic image lines comprising the steps of:

identifying said characteristic in one of said ultrasonic image lines;

determining the velocity of said characteristic in said one of said ultrasonic image lines; and using said velocity to identify said characteristic in another of said ultrasonic image lines.

2. In the ultrasonic diagnostic imaging system of claim 1, wherein said time sequential ultrasonic image lines comprise lines of an M-mode display.

3. In the ultrasonic diagnostic imaging system of claim 2, wherein said time sequential ultrasonic image lines comprise greyscale lines of an M-mode display.

4. The method of claim 1, wherein said characteristic comprises a tissue boundary.

5. The method of claim 1, 2, or 4, wherein said velocity is determined by an ultrasonic Doppler technique.

6. The method of claim 5, wherein said velocity is determined in close time proximity to the acquisition of one of said ultrasonic image lines.

7. The method of claim 3, wherein said velocity is determined from Doppler M-line data.

8. The method of claim 7, wherein said greyscale lines and said Doppler M-line data are acquired in a time interleaved sequence.

9. In an ultrasonic diagnostic imaging system, apparatus for tracking a characteristic of moving objects in the body comprising:

means for acquiring a plurality of temporally different echoes of an object;

means for identifying a characteristic of said object in one of said echoes;

means for determining the velocity of said characteristic; and means for using said velocity to identify said characteristic in a temporally different echo.

10. In the ultrasonic diagnostic imaging system of claim 9, wherein said means for acquiring comprises means for acquiring lines of an M-mode display.

11. In the ultrasonic diagnostic imaging system of claim 9, wherein said means for identifying includes a user controlled cursor.

12. In the ultrasonic diagnostic imaging system of claim 9, wherein said means for determining the velocity comprises a Doppler signal processor.

13. A method for tracking a tissue boundary in an ultrasonic M-mode display of greyscale M-lines comprising the steps of:
produce a map of edge characteristics from said greyscale M-lines;
producing a map of velocity values corresponding to said map of edge characteristics;
denoting a tissue boundary to be traced;
relating said denoted tissue boundary to an edge characteristic; and using velocity values corresponding to the edge characteristics of said denoted tissue boundary to track said denoted tissue boundary.

14. The method of claim 13, wherein said step of producing an edge map comprises detecting the variance of the mean level along each M-line.

15. The method of claim 13, wherein said step of producing a map of velocity values comprises acquiring a sequence of Doppler M-lines.

16. The method of claim 15, wherein said Doppler M-lines are acquired in a time interleaved sequence with said greyscale M-lines.

17. The method of claim 13, further comprising the step of reducing noise in said greyscale M-lines.

18. The method of claim 17, wherein said step of reducing noise comprises performing the mathematical morphologic operations of dilation and erosion on each M-line.

19. In a diagnostic ultrasound system, including means for acquiring M-mode lines of tissue of the body, apparatus for tracing a tissue boundary in an M-mode image comprising:
means for processing said M-mode lines to define the edges of tissue in said lines; and
means, responsive to said defined tissue edges, for tracing a tissue boundary across a plurality of said lines.

20. In a diagnostic ultrasound system, including means for acquiring M-mode lines of tissue of the body, apparatus for tracing a tissue boundary in an M-mode image comprising:
means for processing said M-mode lines to define the edges of tissue in said lines; and
means, responsive to said defined tissue edges, for tracing a tissue boundary across a plurality of said lines,
wherein said processing means comprises means for computing the variance of the mean value of data points along said lines.

21. In a diagnostic ultrasound system,including means for acquiring M-mode lines of tissue of the body, apparatus for tracing a tissue boundary in an M-mode image comprising:
means for processing said M-mode lines to define the edges of tissue in said lines; and
means, responsive to said defined tissue edges, for tracing a tissue boundary across a plurality of said lines,
wherein said M-mode lines comprise lines of greyscale data, and further comprising means for producing a velocity map corresponding to said M-mode lines.

22. The diagnostic ultrasound system of claim 21, wherein said tracing means is further responsive to said velocity map for tracing a tissue boundary.

23. The diagnostic ultrasound system of claim 22, wherein said velocity map comprises Doppler M-mode lines corresponding to said lines of greyscale data.

24. The diagnostic ultrasound system of claim 19 or 22, further comprising means for reducing noise in said lines of greyscale data.

25. In a diagnostic ultrasound system, a method for tracking a characteristic of moving tissue through a temporally acquired sequence of two dimensional ultrasonic images comprising the steps of:
identifying said characteristic in one of said ultrasonic images;
obtaining the velocity of said identified characteristic; and
using said velocity to identify said characteristic in another of said ultrasonic images.

26. In the diagnostic ultrasound system of claim 25, wherein the step of obtaining the velocity of said identified characteristic of said one of said ultrasonic images comprises obtaining said velocity by means of ultrasonic Doppler processing.

27. In the diagnostic ultrasound system of claim 26, wherein said velocity is obtained at approximately the time of acquisition of said one of said ultrasonic images.

28. In a diagnostic ultrasonic imaging system, apparatus for diagnosing the human cardiovascular system comprising:
a processing system for producing an M-mode display of temporally acquired A-line data;
a processing system for producing an M-mode display of temporally acquired Doppler data temporally corresponding to said A-line data;
a tracing system for producing a trace of an image characteristic of said M-mode display of A-line data; and
display means, responsive to said trace, for displaying said trace on said M-mode display of Doppler data.

29. In the diagnostic ultrasonic imaging system of claim 28, further comprising analysis software, responsive to said trace, for performing analysis of the information of said M-mode display of Doppler data.

30. In a diagnostic ultrasound system, a method for tracking a characteristic of moving tissue in a three dimensional voxel image comprising the steps of:
identifying said characteristic in one of the voxels of said three dimensional image;
obtaining the velocity of said identified characteristic; and
using said velocity to identify said characteristic in another of said image voxels.

31. The method of claim 30, wherein said three dimensional voxel image comprises a three dimensional M-mode image.

32. A method for tracking a tissue boundary in an ultrasonic color M-mode display of Doppler M-lines comprising the steps of:
producing a map of edge characteristics from said Doppler M-lines;
denoting a tissue boundary to be traced;
relating said denoted tissue boundary to an edge characteristic; and
using velocity values corresponding to the edge characteristics of said denoted tissue boundary to track said denoted tissue boundary by anticipating successive edge characteristics on the basis of the speed or direction of edge characteristic motion.

33. The method of claim 32, wherein said Doppler M-lines contain velocity information, and wherein said velocity information is used to track said denoted tissue boundary.

34. The method of claim 32, wherein said Doppler M-lines contain Doppler signal intensity information.

35. In a diagnostic ultrasound system, including means for acquiring M-mode lines of tissue of the body, apparatus for tracing a tissue boundary in an M-mode image comprising:

means for initiating the tracing of a tissue boundary in said image in a first direction;

means for initiating the tracing of said tissue boundary in said image in a second direction which is opposite to the first direction; and means for combining said tracings to define the tissue boundary.

36. In the diagnostic ultrasound system of claim 35, wherein said combining means further comprises means for combining said tracings on a weighted basis.

37. In the diagnostic ultrasound system of claim 36, wherein said combining means further comprises means for combining said tracings on a weighted basis as a function of the proximity of a trace from its point of initiation.

38. In the diagnostic ultrasound system of claim 35, wherein said means for initiating the tracing of a tissue boundary in said image in a first direction further comprises means for initiating the tracing of a tissue boundary in a first direction from one side of said image; and wherein said means for initiating the tracing of said tissue boundary in said image in a second direction further comprises means for initiating the tracing of a tissue boundary in a second direction from the other side of said image.

39. In the diagnostic ultrasound system of claim 35, wherein each of said means for initiating a tracing comprises means for utilizing ultrasonic motion signals to trace a tissue boundary.

40. In the diagnostic ultrasound system of claim 39, wherein said ultrasonic motion signals comprise Doppler velocity signals.

41. In an ultrasonic diagnostic imaging system, a method for tracking a characteristic of moving objects in the body comprising:

acquiring a plurality of temporally different B-mode echoes of an object;

identifying a characteristic of said object in one of said B-mode echoes;

determining the velocity of said characteristic by the Doppler method; and using the direction of said velocity of said one of said B-mode echoes to identify the location of said characteristic in a temporally different B-mode echo.

* * * * *